United States Patent [19]
Teramoto et al.

[11] Patent Number: 5,900,482
[45] Date of Patent: May 4, 1999

[54] PROCESS FOR THE PREPARATION OF ε-CAPROLACTAM

[75] Inventors: Kouji Teramoto; Yu Kanda; Makoto Tezuka; Toshio Uchibori; Hidefumi Sano, all of Kitakyushu, Japan

[73] Assignee: Mitsubishi Chemical Corporation, Tokyo, Japan

[21] Appl. No.: 08/820,095

[22] Filed: Mar. 19, 1997

Related U.S. Application Data

[63] Continuation-in-part of application No. PCT/JP96/02015, Jul. 19, 1996.

[51] Int. Cl.$^6$ .................................................. C07D 201/04
[52] U.S. Cl. ........................................... 540/535; 540/536
[58] Field of Search ...................... 540/535, 536

[56] References Cited

U.S. PATENT DOCUMENTS

| | | | |
|---|---|---|---|
| 4,140,685 | 2/1979 | Goettsch et al. | 260/239.3 |
| 4,457,807 | 7/1984 | Rulkens et al. | 203/72 |

OTHER PUBLICATIONS

Patent Abstracts of Japan, JP–8–176102, Jul. 9, 1996.
Patent Abstracts of Japan, JP–8–193061, Jul. 30, 1996.
Patent Abstracts of Japan, JP–8–193062, Jul. 30, 1996.
Patent Abstracts of Japan, JP–8–198845, Aug. 6, 1996.
Patent Abstracts of Japan, JP–5–301858, Nov. 16, 1993.

*Primary Examiner*—Mukund J. Shah
*Assistant Examiner*—Bruck Kifle
*Attorney, Agent, or Firm*—Oblon, Spivak, McClelland, Maier & Neustadt, P.C.

[57] ABSTRACT

The present invention provides a method for producing ε-caprolactam, which comprises subjecting cyclohexene to a hydration reaction to obtain cyclohexanol, subjecting the cyclohexanol to a dehydrogenation reaction to obtain cyclohexanone, subjecting the cyclohexanone to an oxime-forming reaction to obtain cyclohexanone oxime, and subjecting the cyclohexanone oxime to a Beckmann rearrangement reaction to obtain ε-caprolactam, wherein methylcyclopentanones contained in the cyclohexanone subjected to the oxime-forming reaction are controlled to be not more than 400 ppm.

According to the present invention, it is possible to produce ε-caprolactam having a quality not inferior to conventional quality at a low cost.

10 Claims, No Drawings

PROCESS FOR THE PREPARATION OF ε-CAPROLACTAM

This application is a continuation-in-part of PCT Patent application No. PCT/JP96/02015 filed Jul. 19, 1996 and incorporated entirely herein by reference.

TECHNICAL FIELD

The present invention relates to a method for producing ε-caprolactam from cyclohexene as the starting material. More particularly, it relates to a method for producing ε-caprolactam, which comprises subjecting cyclohexene to a hydration reaction to cyclohexanol, subjecting the cyclohexanol to a dehydrogenation reaction to obtain cyclohexanone, subjecting the cyclohexanone to an oxime-forming reaction to obtain cyclohexanone oxime and finally subjecting the cyclohexanone oxime to a Beckmann rearrangement reaction to obtain ε-caprolactam.

BACKGROUND ART

ε-Caprolactam has been produced mainly by converting cyclohexanone to an oxime, and subjecting the formed cyclohexanone oxime to a Beckmann rearrangement. The cyclohexanone oxime is usually produced by reacting cyclohexanone with hydroxylamine.

Heretofore, for the production of cyclohexanone which is useful for producing ε-caprolactam, it has been most common to employ a method which comprises oxidizing cyclohexane with molecular oxygen to obtain a mixture of cyclohexanol and cyclohexanone, separating cyclohexanol and cyclohexanone by distillation and converting the separated cyclohexanol to cyclohexanone by a dehydrogenation reaction, as an industrially practiced method. Also known is a method wherein phenol is subjected to hydrogenation and dehydrogenation to obtain cyclohexanone.

On the other hand, an attention has been drawn in recent years to a method of hydrating cyclohexene in the presence of a solid catalyst, particularly a zeolite catalyst, as a method for producing cyclohexanol on an industrial scale. Many reports have been made on such a method since about 1965, but a production on an industrial scale has only recently been realized (Chemical Economy, 1993 March issue, p. 40–45).

DISCLOSURE OF THE INVENTION

The method for producing cyclohexanol by hydrating cyclohexene is an advantageous method from the viewpoint of production costs and is one of preferred methods for producing cyclohexanol. Accordingly, it is considered to be industrially advantageous if the cyclohexanol produced by such a method can be utilized as the starting material for the production of ε-caprolactam.

Under these circumstances, the present inventors have conducted a study on the possibility of producing ε-caprolactam by using the cyclohexanol obtained by such a method and as a result, it has been found that as is different from ε-caprolactam produced from cyclohexanol obtained by other methods, there is a problem specific to such a method with respect to the quality.

Usually, to produce ε-caprolactam by using the cyclohexanol obtained by the hydration reaction of cyclohexene, as the starting material, many steps are required, and various by-products will form, whereby it is very difficult to judge which by-products at which production steps should be particularly taken into accounts.

The present inventors have conducted extensive studies on the above problem and as a result, have found it possible to solve the problem by controlling specifically the amount of certain specific impurities in the cyclohexanone as the starting material in the oxime-forming reaction step in the production of ε-caprolactam using cyclohexene as the starting material. The present invention has been accomplished on the basis of this discovery.

That is, the present invention provides a method for producing ε-caprolactam, which comprises subjecting cyclohexene to a hydration reaction to obtain cyclohexanol, subjecting the cyclohexanol to a dehydrogenation reaction to obtain cyclohexanone, subjecting the cyclohexanone to an oxime-forming reaction to obtain cyclohexanone oxime, and subjecting the cyclohexanone oxime to a Beckmann rearrangement reaction to obtain ε-caprolactam, wherein methylcyclopentanones contained in the cyclohexanone subjected to the oxime-forming reaction are controlled to be not more than 400 ppm.

Now, the present invention will be described in detail.

In the method of the present invention, firstly, cyclohexene and water are reacted to obtain cyclohexanol. The hydration reaction of cyclohexene is usually carried out by means of a solid acid catalyst, sulfuric acid, hydrochloric acid, phosphoric acid, an aromatic sulfonic acid or the like, as the catalyst. It is particularly preferred to employ a solid acid catalyst. As the solid acid catalyst, a zeolite or an ion exchange resin may, for example, usually be mentioned. A zeolite is particularly preferred. As such a zeolite, various zeolites such as crystalline aluminosilicate, aluminometallosilicate and metallosilicate, may be used. Particularly preferred is a pentacyl-type aluminosilicate or metallosilicate. The metal contained in the metallosilicate may, for example, be a metal element such as titanium, gallium, iron, chromium, zirconium or hafnium. Among them, gallium is particularly preferred.

The hydration reaction is carried out by a conventional method such as a fluidized bed system, a agitation batch system or a continuous system. In the case of a continuous system, either a catalyst-packed continuous flow system or an agitation tank flow system may be employed. The temperature for the reaction is preferably low from the viewpoint of the equilibrium in the hydration reaction of cyclohexene or the prevention of side reactions and high from the viewpoint of the reaction rate. The optimum temperature varies also depending upon the nature of the catalyst, but is usually selected within a range of from 50 to 250° C., preferably from 80 to 200° C.

The obtained cyclohexanol is subjected to a dehydrogenation reaction to obtain cyclohexanone. The dehydrogenation reaction of cyclohexanol may be carried out by any conventional method. Usually, it is carried out by heating in the presence of a dehydrogenation catalyst usually at a temperature of from 150 to 750° C., preferably from 200 to 450° C. As the dehydrogenation catalyst, a metal such as nickel, cobalt, platinum, zinc, calcium, chromium or copper, or its oxide, may, for example, be mentioned. A mixture thereof may also be employed. Preferably, it is a metal oxide catalyst such as zinc oxide, calcium oxide, chromium oxide or copper oxide. Further, such a catalyst may be supported on a carrier such as alumina. This reaction is an equilibrium reaction, and the product is obtained in the form of a mixture of cyclohexanone and cyclohexanol. Therefore, cyclohexanone and cyclohexanol are separated by e.g. distillation, and the separated cyclohexanol is re-used as the starting material for the dehydrogenation reaction.

The cyclohexanone thus obtained, contains a small amount of methylcyclopentanones, to which no particular attention has been paid. These impurities undergo reactions as the lactam-forming reaction proceeds and will be changed into substances which can hardly be separated from ε-caprolactam, and consequently they will be included in the ε-caprolactam product and thus impair the product quality.

Accordingly, the method for producing ε-caprolactam from cyclohexene as the starting material of the present invention, is characterized in that methylcyclopentanones contained in the cyclohexanone subjected to the oxime-forming reaction are controlled to be at most 400 ppm, preferably at most 300 ppm, more preferably from 5 to 100 ppm. In the present invention, the amount of methylcyclopentanones is the total amount of 2-methylcyclopentanone and 3-methylcyclopentanone. If the subsequent step is carried out by using cyclohexanone wherein methylcyclopentanones exceed 400 ppm, as the starting material, to obtain ε-caprolactam, it will be impossible to remove impurities derived from methylcyclopentanones, as mentioned above, whereby it will be difficult to obtain ε-caprolactam having a satisfactory product quality. From the viewpoint of the product quality of ε-caprolactam, the smaller the content of methylcyclopentanones in the cyclohexanone, the better. However, the content of methylcyclopentanones may be set appropriately depending upon the balance between the desired product quality of ε-caprolactam and the work load required for the operation for separating methylcyclopentanones, and it is usually not required to completely remove methylcyclopentanones.

To obtain cyclohexanone wherein methylcyclopentanones are not more than 400 ppm, a method may be employed wherein the starting material, the catalyst and the reaction conditions for the dehydrogenation reaction of cyclohexanol are strictly controlled so that methylcyclopentanones will be not more than 400 ppm, or a method may be employed wherein cyclohexanone obtained by the dehydrogenation reaction, is purified by e.g. distillation.

Further, methylcyclopentanones are believed to have formed as a result of dehydrogenation of a very small amount of methylcyclopetanols formed as by-products by a rearrangement reaction at the time of hydration of cyclohexene to obtain cyclohexanol. Accordingly, it is an effective method to preliminarily reduce the amount of methylcyclopentanols in the cyclohexanol subjected to the dehydrogenation reaction. Methylcyclopentanols in the cyclohexanol are preferably not more than 200 ppm, more preferably not more than 150 ppm. In such a case, the methylcyclopentanols mean the total amount of 2-methylcyclopentanol and 3-methylcyclopentanol.

Further, as the cyclohexanone subjected to the oxime-forming reaction, it is preferred to employ the one wherein cyclopentacarboaldehyde is not more than 50 ppm. By using such cyclohexanone, it is possible to obtain ε-caprolactam of still higher quality.

Furthermore, in order to obtain caprolactam of a high purity, the cyclohexanone subjected to the oxime-forming reaction is preferably the one having the content of cyclohexanol as an unreacted starting material reduced usually to a level of not more than 1000 ppm, preferably not more than 600 ppm, by e.g. distillation.

The cyclohexanone wherein methylcyclopentanones are not more than 400 ppm, thus obtained, is subjected to the oxime-forming reaction under a known reaction condition to obtain cyclohexanone oxime. The oxime-forming reaction is usually carried out by reacting cyclohexanone with hydroxylamine to obtain cyclohexanone oxime. Hydroxylamine is an unstable compound by itself. Therefore, it is employed usually in the form of a sulfate or nitrate of hydroxylamine. For example, cyclohexanone and hydroxylamine sulfate are reacted in an aqueous solution or a non-aqueous solution. The oxime-forming reaction is not limited to the reaction with hydroxylamine, and cyclohexanone oxime may be obtained, for example, by a method wherein cyclohexanone is reacted with nitrogen monoxide and hydrogen in the presence of a platinum group catalyst (U.S. Pat. No. 4,929,756) or a method wherein cyclohexanone is reacted with ammonia in the presence of hydrogen peroxide (U.S. Pat. No. 4,745,221).

Then, the above cyclohexanone oxime is subjected to a Beckmann rearrangement by a known method to obtain ε-caprolactam. For example, it is possible to employ a method wherein the cyclohexanone oxime is subjected to a Beckmann rearrangement in concentrated sulfuric acid or fuming sulfuric acid to obtain ε-caprolactam sulfate, which is then neutralized with a base such as ammonia, or a method wherein the cyclohexanone oxime is subjected to a Beckmann rearrangement in a gas phase or in a liquid phase in the presence of a solid acid catalyst, or a method wherein the Beckmann rearrangement is carried out in a state where the catalyst is uniformly dissolved in a liquid phase. When the cyclohexanone oxime is contacted with sulfuric acid or fuming sulfuric acid, the amount of sulfuric acid or fuming sulfuric acid relative to the cyclohexanone oxime is usually from 1.0 to 2.0 by a molar ratio. It is usually preferred to contact the cyclohexanone oxime with fuming sulfuric acid. The concentration of free sulfur trioxide in the fuming sulfuric acid is usually from 1 to 30 wt %. The reaction temperature for the Beckmann rearrangement is usually from 60 to 130° C., preferably from 70 to 100° C. If the temperature is low, side reactions can be suppressed on one hand, but the viscosity increases to make mixing inadequate on the other hand. The suppression of side reactions improves the yield, while the inadequate mixing decreases the yield. Accordingly, when the temperature is low, it is advisable to increase the stirring power. This reaction is an exothermic reaction and thus is usually carried out while removing the heat. Such heat removal may be carried out by circulating the reaction solution externally and/or by providing a jacket having cooling water circulated therein. The Beckmann rearrangement can be carried out in one step or in a plurality of steps. Further, the reaction solution subjected to the Beckmann rearrangement may be subjected to heat treatment usually at a temperature of from 130 to 200° C. for from 0.1 to 10 hours to decompose impurities and to improve the product quality. In either method, the resulting ε-caprolactam may be purified by distillation or crystallization to obtain a final product.

BEST MODE FOR CARRYING OUT THE INVENTION

Now, the present invention will be described in further detail with reference to Examples. However, it should be understood that the present invention is by no means restricted by such specific Examples. The quantitative analyses of methylcyclopentanones in the cyclohexanone or methylcyclopentanols in the methyl- or cyclohexanol, were carried out by gas chromatography employing a capillary column.

EXAMPLE 1

(1) Hydration reaction of cyclohexene

Into an autoclave equipped with a stirrer, gallium silicate (atomic ratio of $SiO_2/Ga_2O_3=50/1$) as a catalyst, 15 parts by weight of cyclohexene, 30 parts by weight of water, and 10 parts by weight of a hydration reaction catalyst were introduced and reacted in a nitrogen atmosphere at 120° C. for one hour to obtain a cyclohexanol mixture. The yield of cyclohexanol was 10.8%.

(2) Purification of cyclohexanol

The obtained cyclohexanol mixture was purified by a rectifying tower with 10 plates. This purified cyclohexanol contained methylcyclopentanols in a total amount of 500 ppm.

(3) Dehydrogenation reaction of cyclohexanol

The purified cyclohexanol was vaporized and supplied to a tubular reactor packed with a copper oxide-chromium oxide catalyst and set at 250° C. under a reaction pressure of 0.17 MPa at GHSV (gas space velocity) of 2.4 $hr^{-1}$ to carry out the dehydrogenation reaction. The yield of cyclohexanone was 60%.

(4) Purification of cyclohexanone

The obtained reaction solution was purified by the following distillation operation until the purity of cyclohexanone became at least 99.5%.

First tower: Low boiling components are removed by batch distillation by a tower with a plate number of 30 plates and at a reflux ratio of 20.

Second tower: Purification of cyclohexanone is carried out by continuous distillation by a tower with a plate number of 40 plates and at a reflux ratio of 10.

Third tower: Purification of cyclohexanone is carried out by batch distillation by a tower with a plate number of 30 plates.

The contents of 2-methylcyclopentanone, 3-methylcyclopentanone and cyclopentane carboaldehyde in the above purified cyclohexanone were 5 ppm, 31 ppm and 5 ppm, respectively.

(5) Production of cyclohexanone oxime

A 45% hydroxylamine sulfate aqueous solution charged into a jacketed agitation tank, was heated to 85° C., and the purified cyclohexanone was dropwise added. At that time, aqueous ammonia was simultaneously dropwise added, so that the pH of the reaction solution became from 4.0 to 4.5. After completion of the dropwise addition of cyclohexanone, an excess 45% hydroxylamine sulfate aqueous solution was further added thereto, followed by stirring for 30 minutes, to complete the reaction. Then, the reaction solution was left to stand for separation, whereupon the oil phase was collected as cyclohexanone oxime. Water contained in the cyclohexanone oxime was removed under reduced pressure.

(6) Beckmann rearrangement

The cyclohexanone oxime and 25% fuming sulfuric acid were simultaneously dropwise added to a jacketed agitation tank, so that the acidity (the weight ratio of the fuming sulfuric acid based on the total amount of the fuming sulfuric acid and the cyclohexanone oxime) of the Beckmann rearrangement solution became 57%, the free $SO_3$ concentration became 7.5%, and the residence time in the reactor became 1 hour. At that time, in order to suppress local heat generation, stirring was carried out at a stirring speed of at least 1000 rpm, and cooling water was circulated into the jacket to maintain the reaction temperature at a level of from 70 to 100° C.

(7) $SO_3$ treatment

The Beckmann rearrangement solution thus obtained was transferred to a jacketed agitation tank (500 ml), and treated at a treating temperature of from 90 to 125° C. for 2 hours while maintaining the $SO_3$ concentration at a level of from 7 to 7.5% with stirring at a stirring speed of at least 300 rpm to obtain a $SO_3$ treatment solution.

(8) Post treatment

The obtained $SO_3$ treatment solution was neutralized with aqueous ammonia. The neutralization reaction was carried out at a neutralization temperature of 70° C. at a pH of from 7.0 to 7.5 by circulating hot water to the jacketed agitation tank. Then, the neutralized solution was extracted with benzene for three times in total. The extraction was carried out by introducing the neutralized solution and benzene into a separating funnel, shaking them for 10 minutes, and then leaving them to stand still for 5 minutes, whereupon the oil phase was collected, while the aqueous phase was again extracted with benzene. Here, the amount of benzene was adjusted so that the ε-caprolactam concentration as a theoretical amount became from 15 to 20 wt %. The extract solutions thus obtained were stirred and mixed at 40° C. and then left to stand for 30 minutes, whereupon the aqueous phase was again separated.

A proper amount of sodium hydroxide was added to the obtained ε-caprolactam/benzene liquid, and benzene was distilled off under reduced pressure to obtain crude ε-caprolactam. The distillation was carried out in such a manner that the initial fraction of 10 wt %, the main fraction of 80 wt % and the residue of 10 wt % were collected as three portions, whereupon the main fraction and the residue (aqueous ammonium sulfate solution) were used for the evaluation of the product quality. The results are shown in Table 1.

(9) Method for evaluating the product quality of ε-caprolactam

The product quality of the obtained ε-caprolactam was evaluated on the basis of the following four standards. The obtained results are shown in Table 1.

PZ (potassium permanganate value)

1 g of the ε-caprolactam sample was dissolved in 100 ml of water, and 1 ml of a 0.01N potassium permanganate aqueous solution was added thereto. The mixture was stirred, whereby the time (seconds) until the color became the same as the color of the comparative standard solution (3.0 g of cobalt chloride ($CoCl_2.6H_2O$) and 2.00 g of copper sulfate ($CuSO_4.5H_2O$) were diluted with water to 100 ml), was measured.

PM (amount of consumption of permanganate)

A solution having 100 g of ε-caprolactam dissolved in 150 ml of 8M sulfuric acid, was titrated with a 0.1N potassium permanganate aqueous solution, whereby the amount of consumption of potassium permanganate was measured and represented by a unit of ml/kg·ε-caprolactam.

VB (volatile base)

50 g of ε-caprolactam was dissolved in 400 ml of a 2N sodium hydroxide aqueous solution, and the solution was boiled for one hour, whereby the generated decomposition gas and distilled water are blown into 500 ml of deionized water having 4 ml of a 0.02N sulfuric acid aqueous solution dissolved therein. Then, this deionized water was titrated with 0.1N sodium hydroxide, whereby the reduced amount of sulfuric acid was calculated as ammonia.

Ammonium sulfate quality

The pH of the ammonium sulfate aqueous solution was adjusted to 5.2 with 8M sulfuric acid. 5 ml of the adjusted sample was diluted to 500 ml, and this diluted solution was put into a quartz cell of 10 mm, and the absorbance at a wavelength of 255 nm was measured. Control: Deionized water, ammonium sulfate quality=absorbance×dilution ratio

EXAMPLE 2

The operation was carried out in the same manner as in Example 1 except that rectification of cyclohexanol in step (2) was not carried out, and in the purification step of cyclohexanone in step (4), the distillation condition of the first tower was changed so that the total amount of low boiling point components in the cyclohexanone became 0.12% and no distillation by the third tower was carried out. The results are shown in Table 1.

Here, the above purified cyclohexanone contained 110 ppm of 2-methylcyclopentanone, 180 ppm of 3-methylcyclopentanone and 30 ppm of cyclopentane carboaldehyde.

Comparative Example 1

The operation was carried out in the same manner as in Example 2 except that in the purification step of cyclohexanone in step (4), no distillation by the first tower was carried out. The results are shown in Table 2. Here, the above purified cyclohexanone contained 210 ppm of 2-methylcyclopetanone, 280 ppm of 3-methylcyclopentanone and 87 ppm of cyclopentane carboaldehyde.

Comparative Example 2

The operation was carried out in the same manner as in Example 1 except that using cyclohexanol obtained by oxidation of cyclohexane, 27% of low boiling point components were removed by distillation purification by a rectifying tower of 30 plates at a reflux ratio of 30, and the quality of $\epsilon$-caprolactam was evaluated.

The results are shown in Table 2.

In the purified cyclohexanone, none of 2-methylcyclopetanone, 3-methylcyclopentanone and cyclopentane carboaldehyde was detected.

Comparative Example 3

The operation was carried out in the same manner as in Example 1 except that using cyclohexanol obtained by oxidation of cyclohexane, 12% of low boiling point components were removed by distillation purification by a rectifying tower with 30 plates at a reflux ratio of 30, and the quality of $\epsilon$-caprolactam was evaluated. The results are shown in Table 2.

Here, in the purified cyclohexanone, none of 2-methylcyclopentanone, 3-methylcyclopentanone and cyclopentane carboaldehyde was detected.

TABLE 1

|  | Example 1 | Example 2 |
|---|---|---|
| Methylcyclopentanones contained in the cyclohexanone (ppm) | 36 | 290 |
| Cyclopentane carboaldehyde contained in the cyclohexanone (ppm) | 5 | 30 |
| PZ (sec) | 19800 | 14000 |
| PM (mλ/kg · $\epsilon$-caprolactam) | 3.7 | 1.0 |
| VB (ppm) | 3.0 | 3.7 |
| Ammonium sulfate quality | 15 | 33 |

TABLE 2

|  | Comparative Example 1 | Comparative Example 2 | Comparative Example 3 |
|---|---|---|---|
| Methylcyclopentanones contained in the cyclohexanone (ppm) | 490 | Not detected | Not detected |
| Cyclopentane carboaldehyde contained in the cyclohexanone (ppm) | 87 | Not detected | Not detected |
| PZ (sec) | 9500 | 18000 | 18000 |
| PM (mλ/kg · $\epsilon$-caprolactam) | 4.2 | — | — |
| VB (ppm) | 6.2 | 3.0 | 7.7 |
| Ammonium sulfate quality | 15 | — | — |

Tables 1 and 2, it is evident that by using the one wherein methylcyclopentanones in the cyclohexanone are at most 400 ppm, or the one wherein cyclopentane carboaldehyde is not more than 50 ppm, it is possible to obtain $\epsilon$-caprolactam of a high quality, which in turn leads to improvement in the product quality of ammonium sulfate which is simultaneously produced as a by-product.

Such an effect obtained by using a specific cyclohexanone having a low content of impurities, is particularly remarkable when cyclohexene is used as the starting material. Further, the ammonium sulfate quality is related to the product quality of $\epsilon$-caprolactam. Namely, if the product quality of ammonium sulfate is poor, if an attempt to improve it is made, the product quality of $\epsilon$-caprolactam will further deteriorate. In other words, even when the evaluation of the quality of $\epsilon$-caprolactam is the same, the quality of $\epsilon$-caprolactam as a whole will be evaluated to be poor if the ammonium sulfate quality is poor.

EXAMPLE 3

The operation was carried out in the same manner as in Example 1 except that the purified cyclohexanol obtained in step (2) was further purified to a purity of at least 99.99% by a tower with 30 plates and then subjected to dehydrogenation, and commercially available 2-methylcyclopentanone and 3-methylcyclopentanone were added in a ratio of about 1:1 to the cyclohexanone purified in step (4) so that the total amount became 380 ppm. The results are shown in Table 3.

Comparative Example 4

The operation was carried out in the same manner as in Example 3 except that the concentration of methylcyclopentanones in the cyclohexanone was adjusted to 1000 ppm. The results are shown in Table 3.

TABLE 3

|  | Example 3 | Comparative Example 4 |
|---|---|---|
| Methylcyclopentanones contained in the cyclohexanone (ppm) | 380 | 1000 |
| PZ (sec) | 18700 | 18700 |
| PM (mλ/kg · $\epsilon$-caprolactam) | 2.2 | 2.7 |
| VB (ppm) | 3.2 | 3.3 |
| Ammonium sulfate quality | 17 | 23 |

From Table 3, it is evident that even when using a highly pure cyclohexanone as a starting material, if methylcyclopentanones are present even in a minor amount in the cyclohexanone, the methylcyclopentanones adversely affect the quality of $\epsilon$-caprolactam, particularly the ammonium sulfate quality.

EXAMPLE 4

The operation was carried out in the same manner as in Example 1 except that the purified cyclohexanol obtained in step (2) was further purified to a purity of at least 99.99% by a tower with 30 plates and then subjected to dehydrogenation, and commercially available cyclopentane carboaldehyde was added thereto so that the concentration of cyclopentane carboaldehyde became 250 ppm. The results are shown in Table 4.

EXAMPLE 5

The operation was carried out in the same manner as in Example 4 except that the concentration of cyclopentacarboaldehyde in the cyclohexanone was adjusted to 350 ppm. The results are shown in Table 4.

TABLE 4

|  | Example 4 | Example 5 |
| --- | --- | --- |
| Cyclopentane carboaldehyde contained in the cyclohexanone (ppm) | 250 | 350 |
| PZ (sec) | 18400 | 18400 |
| PM (mλ/kg · ε-caprolactam) | 2.2 | 1.9 |
| VB (ppm) | 3.1 | 10.7 |

From Table 4, it is evident that cyclopentane carboaldehyde in the cyclohexanone adversely affects the quality of ε-caprolactam, particularly VB.

Industrial Applicability

According to the method of the present invention, ε-caprolactam comparable with the conventional quality can be produced at a low cost using cyclohexene as the starting material, and the method is useful for the industrial purpose.

We claim:

1. A method for producing ε-caprolactam, which comprises subjecting cyclohexene to a hydration reaction to obtain cyclohexanol, subjecting the cyclohexanol to a dehydrogenation reaction to obtain cyclohexanone, subjecting the cyclohexanone to an oxime-forming reaction to obtain cyclohexanone oxime, and subjecting the cyclohexanone oxime to a Beckmann rearrangement reaction to obtain ε-caprolactam, wherein methylcyclopentanones contained in the cyclohexanone subjected to the oxime-forming reaction are controlled to be not more than 400 ppm.

2. The method according to claim 1, wherein cyclopentane carboaldehyde contained in the cyclohexanone subjected to the oxime-forming reaction is controlled to be not more than 50 ppm.

3. The method according to claim 1 or 2, wherein methylcyclopentanols contained in the cyclohexanol subjected to the dehydrogenation reaction are controlled to be not more than 200 ppm.

4. The method according to claim 1, wherein methylcyclopentanones contained in the cyclohexanone subjected to the oxime-forming reaction are controlled to be not more than 300 ppm.

5. The method according to claim 1, wherein methylcyclopentanols contained in the cyclohexanol subjected to the dehydrogenation reaction are controlled to be not more than 150 ppm.

6. The method according to claim 1, wherein a solid acid catalyst is used in the hydration reaction of cyclohexane.

7. The method according to claim 1, wherein a zeolite catalyst is used in the hydration reaction of cyclohexane.

8. The method according to claim 1, wherein the oxime-forming reaction is carried out by reacting the cyclohexanone with hydroxylamine.

9. The method according to claim 1, wherein the cyclohexanone oxime is subjected to the Beckmann rearrangement reaction in sulfuric acid or fuming sulfuric acid to obtain ε-caprolactam sulfate.

10. The method according to claim 1, wherein cyclohexanol in the cyclohexanone supposed to the oxime-forming reaction is controlled to be not more than 1000 ppm.

* * * * *

UNITED STATES PATENT AND TRADEMARK OFFICE
CERTIFICATE OF CORRECTION

PATENT NO. : 5,900,482

DATED : May 4, 1999

INVENTOR(S): Kouji TERAMOTO, et al.

It is certified that an error appears in the above-identified patent and that said Letters Patent is hereby corrected as shown below:

On the title page, item [30] has been omitted. It should be:

--[30]   Foreign Application Priority Data
    Jul. 20, 1995 [JP] Japan .............. 7-184131
    Jul. 20, 1995 [JP] Japan .............. 7-184132--

Signed and Sealed this

Second Day of May, 2000

Attest:

Q. TODD DICKINSON

*Attesting Officer*     *Director of Patents and Trademarks*